(12) United States Patent
Dolbier, Jr. et al.

(10) Patent No.: US 7,652,178 B2
(45) Date of Patent: Jan. 26, 2010

(54) PERFLUOROPARACYCLOPHANE AND METHODS OF SYNTHESIS AND USE THEREOF

(75) Inventors: William R. Dolbier, Jr., Gainesville, FL (US); Puhui Xie, Gainesville, FL (US); Rakesh Kumar, Carmel, IN (US)

(73) Assignee: Specialty Coating Systems, Inc., Indianapolis, IN (US)

( * ) Notice: Subject to any disclaimer, the term of this patent is extended or adjusted under 35 U.S.C. 154(b) by 0 days.

(21) Appl. No.: 11/710,881

(22) Filed: Feb. 26, 2007

(65) Prior Publication Data

US 2008/0207961 A1 Aug. 28, 2008

(51) Int. Cl.
C07C 21/18 (2006.01)
(52) U.S. Cl. ............... 570/126; 570/127; 570/143; 570/144
(58) Field of Classification Search ........... 570/126, 570/127, 143, 144
See application file for complete search history.

(56) References Cited

U.S. PATENT DOCUMENTS

| | | | |
|---|---|---|---|
| 3,246,627 A | 4/1966 | Loeb et al. |
| 3,268,599 A | 8/1966 | Chow |
| 3,274,267 A | 9/1966 | Sui-Wu |
| 3,280,202 A | 10/1966 | Glich |
| 3,297,591 A | 1/1967 | Chow et al. |
| 3,301,707 A | 1/1967 | Loeb et al. |
| 3,332,891 A | 7/1967 | Chow |
| 3,342,754 A | 9/1967 | Gorham |
| 3,405,117 A | 10/1968 | Yeh |
| 3,749,601 A | 7/1973 | Tittle |
| 4,176,209 A | 11/1979 | Baker et al. |
| 4,429,153 A | 1/1984 | Punja |
| 4,734,503 A | 3/1988 | Weigert |
| 4,734,533 A | 3/1988 | Ungarelli et al. |
| 4,761,269 A | 8/1988 | Conger et al. |
| 4,783,561 A | 11/1988 | Pregaglia et al. |
| 4,795,838 A | 1/1989 | Bornengo et al. |
| 4,816,608 A | 3/1989 | Bornengo et al. |
| 4,846,998 A | 7/1989 | Pohl et al. |
| 4,853,488 A | 8/1989 | Ungarelli et al. |
| 4,886,923 A | 12/1989 | Ungarelli et al. |
| 4,924,014 A | 5/1990 | Fuss et al. |
| 5,069,972 A | 12/1991 | Versic |
| 5,094,906 A | 3/1992 | Witzke et al. |
| 5,210,341 A | 5/1993 | Dolbier, Jr. et al. |
| 5,266,349 A | 11/1993 | Bok et al. |
| 5,268,202 A | 12/1993 | You et al. |
| 5,288,504 A | 2/1994 | Versic |
| 5,302,767 A | 4/1994 | Galley et al. |
| 5,368,645 A | 11/1994 | Bok et al. |
| 5,424,097 A | 6/1995 | Olson et al. |
| 5,534,068 A | 7/1996 | Beach et al. |
| 5,536,317 A | 7/1996 | Crain et al. |
| 5,536,319 A | 7/1996 | Wary et al. |
| 5,536,321 A | 7/1996 | Olsen et al. |
| 5,536,322 A | 7/1996 | Wary et al. |
| 5,536,892 A | 7/1996 | Dolbier, Jr. et al. |
| 5,538,758 A | 7/1996 | Beach et al. |
| 5,556,473 A | 9/1996 | Olson et al. |
| 5,669,971 A | 9/1997 | Bok et al. |
| 5,689,027 A | 11/1997 | Abichandani et al. |
| 5,709,753 A | 1/1998 | Olson et al. |
| 5,789,068 A | 8/1998 | King et al. |
| 5,828,132 A | 10/1998 | Eissa |
| 5,841,005 A * | 11/1998 | Dolbier et al. ............ 570/144 |
| 5,849,962 A | 12/1998 | Dolbier, Jr. et al. |
| 5,879,808 A | 3/1999 | Wary et al. |
| 5,886,026 A | 3/1999 | Hunter et al. |
| 5,888,905 A | 3/1999 | Taylor et al. |
| 5,908,506 A | 6/1999 | Olson et al. |
| 6,030,706 A | 2/2000 | Eissa et al. |
| 6,130,096 A | 10/2000 | Tinker et al. |
| 6,150,499 A | 11/2000 | Dolbier, Jr. et al. |
| 6,184,425 B1 | 2/2001 | Kolomeitsev et al. |
| 6,245,760 B1 | 6/2001 | He et al. |
| 6,284,933 B1 | 9/2001 | Dolbier, Jr. et al. |
| 6,362,115 B1 | 3/2002 | Mandal |
| 6,380,415 B2 * | 4/2002 | Uneyama et al. ............ 556/478 |
| 6,392,097 B1 | 5/2002 | Dolbier, Jr. et al. |
| 6,464,740 B1 | 10/2002 | Towery et al. |

(Continued)

FOREIGN PATENT DOCUMENTS

EP 1 262 817 A1 12/2002

(Continued)

OTHER PUBLICATIONS

Dolbier, W. et al., "A Novel, Non-High Dilution Method for Preparation of 1,1,2,2,9,9,10,10-Octafluoro[2.2]paracyclophane", Organic Letters, 2000, 2(13), 1867-1869.*

(Continued)

*Primary Examiner*—Peter G O'Sullivan
*Assistant Examiner*—Sudhakar Katakam
(74) *Attorney, Agent, or Firm*—Lando & Anastasi, LLP

(57) ABSTRACT

A composition comprising perfluoro-[2,2]-paracyclophane dimer compound is disclosed. The synthesis reaction of the paracyclophane dimer from 1,4-bis(chlorodifluoromethane)-2,3,5,6-tetrafluorobenzene involves heating in the presence of a metal catalyst and a solvent. A perfluorinated paraxylylene coating formed from the perfluorinated paracyclophane dimer is also disclosed.

14 Claims, No Drawings

U.S. PATENT DOCUMENTS

| | | |
|---|---|---|
| 6,549,327 B2 | 4/2003 | Foucher et al. |
| 6,559,474 B1 | 5/2003 | Craighead et al. |
| 6,602,932 B2 | 8/2003 | Feldheim et al. |
| 6,646,150 B1 | 11/2003 | Sato et al. |
| 6,667,099 B1 | 12/2003 | Greiner et al. |
| 6,723,143 B2 | 4/2004 | Towery et al. |
| 6,763,576 B2 | 7/2004 | Watchko et al. |
| 6,770,789 B2 | 8/2004 | Dolbier, Jr. et al. |
| 6,780,561 B2 | 8/2004 | Ueda et al. |
| 6,869,698 B2 | 3/2005 | Chen et al. |
| 6,919,484 B2 | 7/2005 | Dolbier, Jr. et al. |
| 6,943,232 B2 | 9/2005 | Blomquist et al. |
| 7,012,165 B2 | 3/2006 | Dolbier, Jr. et al. |
| 7,173,159 B2 | 2/2007 | Ho et al. |
| 2003/0165613 A1 | 9/2003 | Chappa et al. |
| 2003/0228411 A1 | 12/2003 | Tai et al. |
| 2006/0083770 A1 | 4/2006 | Greiner et al. |
| 2007/0009738 A1 | 1/2007 | Kumar |
| 2007/0099019 A1 | 5/2007 | Hanefeld et al. |
| 2007/0148390 A1 | 6/2007 | Kumar |
| 2007/0228606 A1 | 10/2007 | Hanefeld et al. |

FOREIGN PATENT DOCUMENTS

| | | | |
|---|---|---|---|
| JP | 09025252 | | 1/1997 |
| JP | 2002080412 A | * | 3/2002 |
| JP | 2005183729 | | 7/2005 |
| WO | WO 90/02604 A1 | | 3/1990 |
| WO | WO 98/24743 A1 | | 6/1998 |
| WO | WO 99/35111 A1 | | 7/1999 |
| WO | WO 03/055611 A1 | | 7/2003 |
| WO | WO 03/066933 A1 | | 8/2003 |
| WO | WO 2004/065295 A1 | | 8/2004 |

OTHER PUBLICATIONS

CAPLUS English abstract of JP 2002080412 A.*
http://en.wikipedia.org/wiki/Acetonitrile.*
English Translation of Miki et al. (JP2002080412A).*
William R. Dolbier, et al.; An Unprecedented Photodimerization of an Anthraceno [2.2] Paracyclophane, Department of Chemistry, University of Florida, ARKIVOC 2006, p. 97-103.
Solodukhin, S. Yu, et al.; Phenoxydifluoromethyl Substituted Nitrogen Heterocycles, Synthesis and Heterocyclization Reactions of Ethyl 4,4-Difluoro-4-Phenoxyacetoacetate, Molecules 2004, p. 9, 164-169.
S. Clark Ligon, Jr., et al.; First Separation and Characterization of CIS and Trans 1,2-Bisaryloxy Perfluorocyclobutanes, Journal of Fluorine Chemistry 123 (2003) p. 139-146.
H. Amii; The Catalytic Version of Stoichiometric Organic Synthesis, Department of Chemistry, Faculty of Science, Kobe University, Letters in Organic Chemistry, 2005 2, 5-14.
H. Henning Wenk et al., Matrix Isolation and Photochemistry of Tetrafluoro-P-Xylylene, Eur. J. Org. Chem. 1999, pp. 3287-3290.
H. Plenio; The Coordination Chemistry of the CF Unit in Fluorocarbons, Chem Review. 1997, pp. 3363-3384.
Behzad C. Ahvazi, et al. F. Nuclear Magnetic Resonance Spectroscopy for the Elucidation of Carbonyl Groups in Lignins. 1. Model Compounds, J. Argic Food Chem. 1966, 44, 2167-2175.
William R. Dolbier, Jr., et al., Electronic Control of Stereoselectivities of Electrocyclic Reactions of Cyclobutenes: A Triumph of Theory in the Prediction of Organic Reactions, Acc. Chem. Res. 1996, 29, 471-477.
Sushama Mohan Kale, Halogenation and Isomerization Reactions of Aromatics Over K-L, H-Beta and H-ZSM-5 Zeolite Catalysts, Catalysis Division, National Chemical Laboratory, Pune 411 008, India, Apr. 2002.
Derwent Journal of Synthetic Methods, vol. 28, No. 11, 2002 Derwent Information.
Takayuki Shioiri et al., "Use of the aryl groups as the carboxyl synthon. Application to the synthesis of some natural products containing hydroxyl amino acid functions," *Pure & Appl. Chem.*, vol. 66, Nos. 10/11, pp. 2151-2154 (1994).
R. Olson, "Quality Techniques for Optimizing Parylene Conformal Coating", 5 pages, NOVA TRAN® Parylene Coating Services, Indianapolis, IN publication date unknown.
"Solvent Resistance of the Parylene", Abstract, 2001, 8 pages, Specialty Coating Systems, Indianapolis, IN (2001).
L. Wolgemuth, "Assessing the Performance and Suitability of Parylene Coating", *Medical Device & Diagnostic Industry Magazine MDDI Article Index*, Aug. 2000, pp. 1-7.
L. Wolgemuth, "The Surface Modification Properties of Parylene for Medical Applications", *Business Briefing: Medical Device Manufacturing & Technology*, 2002, pp. 1-4.
Parylene Dimer Product Literature, Parylene Coating Services, Inc., publication date unknown.
Properties of Parylene, product literature, Parylene Coating Services, Inc., publication date unknown.
Parylene Conformal Coating Specification and Properties, printed from http://www.scscookson.com/parylene/properties.cfm, publication date unknown.
Zhai, "The Chemistry of 1,1,2,2,9,9,10,10-Octafluoro[2.2] Paracyclophanes," (2005), 189 pages.
Battiste, "4,5-Dehydrooctafluoro[2.2]paracyclophane:facile generation and extraordinary Diels-Alder reactivity," *Tetrahedron Letters*, 43 (2002) 7047-7049.
Murakami, "Molecular recognition by novel cage-type azaparacyclophanes bearing chiral binding sites in aqueous media," *Pure & Appl. Chem.* 65, 3, 551-556 (1993).
Shi-Zheng Zhu, et al., "A convenient preparation of octafluoro[2,2]paracyclophane and dodecafluoro[2,2] paracyclophane," Tetrahedron Letters 43 (2002), pp. 669-671.
Dolbier, Jr., et al., "Synthesis of Perfluoro[2.2]paracyclophane," J. Org. Chem 2008., 73, pp. 2469-2472, (published on Web Feb. 27, 2008).

* cited by examiner

PERFLUOROPARACYCLOPHANE AND METHODS OF SYNTHESIS AND USE THEREOF

BACKGROUND OF THE INVENTION

1. Field of the Invention

This invention relates to paracyclophane compounds, preparation of paracyclophane compounds, and articles comprising polymerized paracyclophane compounds, and more particularly to perfluorinated paracyclophane, synthesis of perfluorinated paracyclophane, as well as articles comprising polymerized perfluorinated paracyclophane.

2. Description of Related Art

Synthesis techniques for preparing fluorinated paracyclophane dimers have been disclosed. For example, Dolbier, Jr. et al., in U.S. Pat. No. 5,841,005, described low dilution techniques for preparing octafluoro-[2,2]-paracyclophane.

Further, polymeric fluorinated parylene, poly-para-xylylene, materials have also been disclosed. For example, Taylor et al., in U.S. Pat. No. 5,888,905, a two-step formation of fluorinated parylene by deposition of a parylene film followed by direct fluorination of the film.

BRIEF SUMMARY OF THE INVENTION

In accordance with one or more aspects of the invention, one or more embodiments thereof involve a composition comprising perfluoro-[2,2]-paracyclophane.

In accordance with still further aspects of the invention, one or more embodiments thereof are directed to a method of preparing a paracyclophane comprising exposing a reaction mixture of a difluoromethyl benzene and at least one metal to conditions that promote formation of a reaction product comprising a perfluoroparacyclophane.

Further embodiments pertinent to other aspects of the invention are directed to a polymer having a formula:

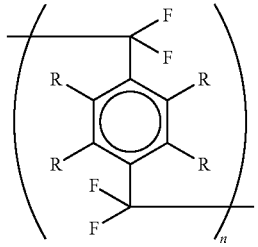

wherein n is at least 2 and R is a halogen.

DETAILED DESCRIPTION

The invention relates to paracyclophane compounds. Some aspects of the invention relate to the preparation of polymeric materials formed from one or more paracyclophane compounds. Still further aspects of the invention relate to articles having parylene polymer on a surface thereof formed from one or more paracyclophane compounds as well as techniques of preparation thereof.

In accordance with one or more embodiments, some compounds and/or polymeric materials relevant to some aspects of the invention pertain to halogenated paracyclophane compounds. For example, the novel compounds, techniques, and materials, including but not limited to polymeric materials, and/or systems of the invention can have one or more halogen-containing moieties. In accordance with some aspects of the invention, the halogenated paracyclophane compounds of the invention can be perfluorinated paracyclophane compounds. Aspects of the invention can involve systems and techniques pertinent to synthesizing perfluorinated paracyclophane compounds.

In accordance with still further embodiments of the invention, the halogenated paracyclophane compounds of the invention can be fluorinated compounds represented by the formula (I).

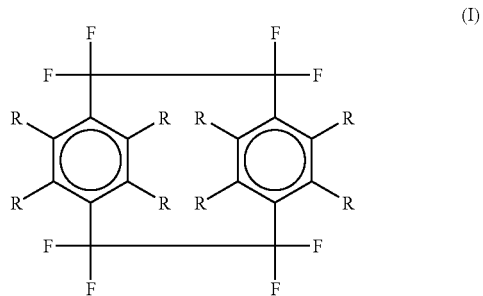

wherein R is a halogen. In some cases, at least one of the moieties that are pendant on the aromatic ring may be fluorine. Indeed, in some cases, some of the fluorinated paracyclophane compounds of the invention are fluorine saturated. In embodiments where the halogen is fluorine, the perfluorinated paracyclophane of some aspects of the invention include perfluoro-[2,2]-paracyclophane.

Some of the aspects pertinent to synthesizing the paracyclophane compounds of the invention can involve providing one or more halogenated precursor compounds. The one or more halogenated precursor compounds can be any suitable compound that includes an aromatic ring having at least one pendant halogen-containing or halogenated moiety. In some cases, the one or more precursor compounds can comprise at least one pendant chlorodihalo-containing moiety such as but not limited to a chlorodifluoroalkyl moiety. Further, the chlorinated precursor compounds of the invention can be an at least partially fluorinated benzene ring having one or more chlorohaloalkyl moieties pendant thereon. Non-limiting examples of the fluorinated or chlorinated precursor compounds of the invention include, but are not limited to, chlorodihaloalkyl fluorinated benzenes, which includes 1,4-bis(chlorodifluoromethyl)-2,3,5,6-tetrafluorobenzene, also referred to as PFPX-dichloride and represented by the formula (II):

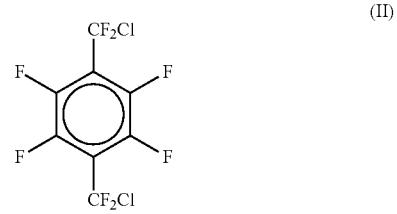

However, the invention is not limited to systems and techniques involving PFPX-dichloride. Other suitable aromatic chlorohaloalkyl compounds may be utilized to prepare the various paracyclophanes of the invention. For example, aromatic compounds having other alkyl-based pendant moieties that provide bridges linking the aromatic rings and facilitate the formation of the fluorinated compounds (I).

The systems and techniques involved in facilitating the synthesis of paracyclophane compounds from halogenated precursor compounds can comprise components, subsystems, or acts that link the ring or aromatic component of the precursor compounds. One or more reduction, rearrangement, substitution, and/or condensation reactions may also be utilized in the schemes of the invention. For example, other reaction schemes may include, for example, pericyclic and redox reactions.

One or more of the fluorinated paracyclophane compounds of the invention may be a reaction product of one or more chlorodihaloalkyl compounds. For example, the synthesis of a fluorinated compound of the invention can involve a reduction, rearrangement, substitution, or condensation reaction of the compound (II).

Any of the reactions of the invention may be catalyzed by one or more compounds which can include one or more salts, metals, organometallic compounds or other complexes such as ligates and chelates, acids, bases, or electron donors or acceptors.

In some cases, one or more of the reactions of the invention may utilize one or more reducing agents that facilitate reduction of, for example, one or more chlorohalomethylated compound to produce a perfluorinated dimer.

Further, any of the reactions of the invention may be facilitated in the presence of one or more solvents or carriers. The solvent, or mixture, is typically an organic solvent, comprising inert compounds that typically do not react with the reactant and the product. The one or more solvents utilized in some aspects of the invention can be aprotic, polar, non-polar, or a hybrid thereof. Non-limiting examples of non-polar solvents that may facilitate one or more reactions of the invention include hexane, benzene, toluene, and chloroform. Non-limiting examples of polar aprotic solvents that may facilitate one or more reactions of the invention include dioxane, tetrahydrofuran, acetone, acetonitrile, dimethyl sulfoxide, and dimethylformamide.

Synthesis of the fluorinated paracyclophanes of the invention can comprise contacting or exposing chlorohalomethyl compounds to conditions that promote formation of a reaction product represented by, for instance, compound (I).

For example, perfluoro-[2,2]-paracyclophane can be prepared through a dimerization reaction of 1,4-bis(chlorodifluoromethyl)-2,3,5,6-tetrafluorobenzene according to the following reaction scheme. The reaction is typically facilitated by one or more reducing agents at an elevated temperature, typically in a range of about 110° C. to about 130° C., and preferably in a range of about 115° C. to about 120° C. The reaction can also be further facilitated by utilizing a solvent. Zinc may be used as a suitable reducing agent and acetonitrile may be used as a solvent to effect formation of the perfluorinated paracyclophane. The reaction is thus typically represented according to scheme (1) below.

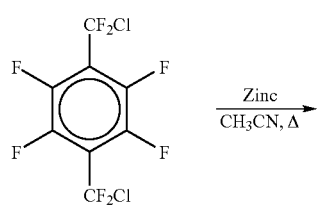

(1)

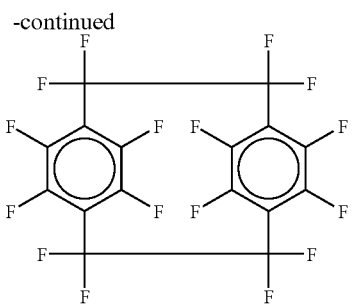

Chlorodihaloalkyl fluorinated compounds of the invention may be prepared by halogenating fluoroxylene compounds. For example, a tetrafluoroxylene may be halogenated to yield chlorohaloalkyl compounds according to scheme (2) below.

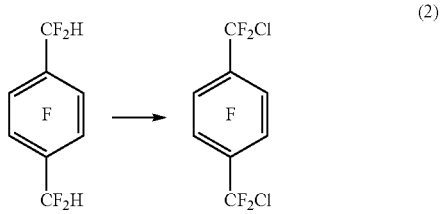

(2)

Scheme (2) can be performed under conditions that thermodynamically promote the formation of the dichloride compound (II). For example, reaction scheme (2) can be facilitated by actinic radiation. Preferred non-limiting embodiments can also utilize one or more solvents such as, but not limited to, carbon tetrachloride, as a medium for one or more reactants.

Tetrafluoroxylene compounds utilized in the above reaction scheme may be synthesized from any suitable precursor compounds. For example, tetrachlorinated cyano compounds may be fluorinated in a substitution reaction to provide a cyano-tetrafluorobenzene intermediate product. The tetrafluorobenzene intermediate compound may then be reduced to provide tetrafluoroaldehyde which can then be further fluorinated by nucleophilic fluorination or fluorodeoxygenation. The compounds of the invention may thus be obtained through the synthetic methodology illustrated in scheme (3) below. Other synthetic schemes may be utilized to prepare the various compounds above. For example, gaseous dicyanobenzene compounds may be converted by activated carbon catalysts at a temperature range of about 280° C. to about 320° C. In some cases, halogen-metal exchange schemes may be appropriate to produce the aldehyde compounds.

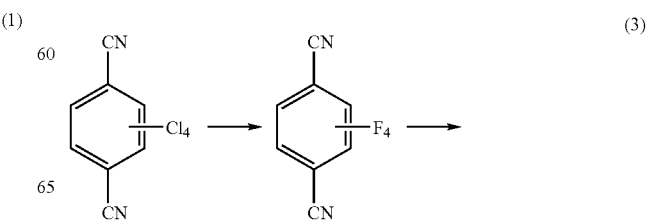

(3)

-continued

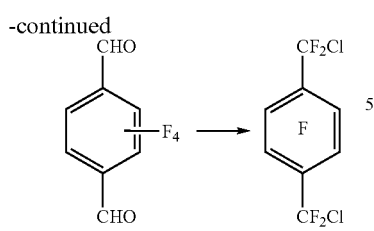

Deposition techniques conventionally utilized with respect to, for example, non-halogenated paracyclophanes, can be utilized to apply one or more layers of the perfluorinated dimer compounds represented by formula (I). Polymerization of the dimer compounds may then provide a perfluorinated polymer. For example, vapor deposition techniques may be utilized to deposit and polymerize a paracyclophane comprising a perfluorinated dimer such as perfluoro-[2,2]-paracyclophane to produce at least one perfluorinated paraxylylene layer on at least a portion of a surface. Other deposition and polymerization techniques may be utilized with the perfluoro-[2,2]-paracyclophane compounds. For example, solvent carrier-based procedures may be utilized to apply a polymerizable layer comprising the perfluorinated dimer compound on the surface. Thereafter, polymerization of the deposited compound comprising perfluorinated paracyclophane may be initiated to produce a perfluorinated paraxylylene layer on the surface. Deposition and polymerization may be performed substantially simultaneously or in substantially the same step. For example, vapor polymerization to produce the perfluorinated paraxylylene may be performed with vaporized perfluoroparacyclophane dimer compound (I).

The paraxylylene polymeric material can be applied on any desired surface or portion of a surface. Thus, the precursor perfluorinated paracyclophane compounds of the invention may be utilized to render any desired surface inert. For example, the paraxylylene polymeric material may be applied on at least a portion of an electronic component such as a semiconductor. Other surfaces include those exposed to or subject chemical and/or biological environments that would damage or otherwise alter the surface properties. Non-limiting examples include components or articles having at least a portion thereof exposed to elevated temperatures, solvents, and/or other corrosive environments. Further, the applied perfluorinated layer may have any desired thickness that provides a desired characteristic. Indeed, the layer may be applied uniformly or at various thickness, alone or with other coatings. The layer can be applied to form a pattern on the surface.

Although various embodiments exemplarily shown have been described, it should be appreciated that the invention is not so limited. This invention is thus not limited in its application to the details of construction and the arrangement of components set forth in the description or illustrated in the drawings.

EXAMPLES

The function and advantages of these and other embodiments of the invention can be further understood from the examples below, which illustrate the benefits and/or advantages of the one or more systems and techniques of the invention but do not exemplify the full scope of the invention.

Example 1

Preparation of 1,4-dicyano-2,3,5,6-tetrafluorobenzene

About 8 g (about 0.03 mol) of 1,4-dicyano-2,3,5,6-tetrachlorobenzene and about 8 g (about 0.137 mol) of KF were transferred into a flask containing about 60 mL of dry dimethyl formamide (DMF).

The mixture was stirred at a temperature of about 110° C. for about ten hours. Nitrogen gas was used to blanket the mixture.

The reaction mixture was poured into a beaker containing about 500 mL ice-water.

The cooled mixture was then to collect the precipitate, which was washed by water and recrystallized with acetone.

The recrystallized product, 1,4-dicyano-2,3,5,6-tetrafluorobenzene, was dried and measured to weigh about 5.4 g (about 90%).

The $^{19}F$ NMR resonance of this product in $CDCl_3$ was δ −128.8 (singlet).

The reaction scheme (4) is illustrated below.

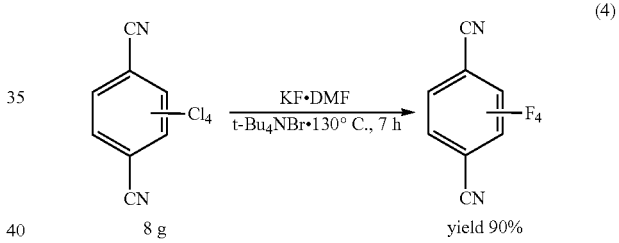

Example 2

Preparation of tetrafluorophthalaldehyde

About 1.25 g (about 6.25 mmol) of the 1,4-dicyano-2,3,5,6-tetrafluorobenzene synthesized according to the procedure described in Example 1 was transferred into about 57.5 mL of $N_2$ bubbled toluene, which was at about 0° C. About 17.5 ml (about 17.5 mmol) of 1 M DIBAL-H (diisopropylaluminumhydride) toluene solution was added. After the reaction mixture was stirred for about 2.5 hours at room temperature, the mixture was cooled to about 0° C.

About 30 mL of about 2 N HCl was added until the pH of the mixture was less than about 2 units.

The aqueous layer was then extracted several times with $CH_2Cl_2$.

The organic layer was combined and dried by evaporation.

The crude product was chromatographed with toluene as a carrier through silica gel and produced about 0.79 g of product (about 62%).

The $^1H$ NMR resonance of this product in $CDCl_3$ was δ 10.36 and the $^{19}F$ NMR resonance was δ −144.1 (singlet).

The reaction scheme (5) is illustrated below.

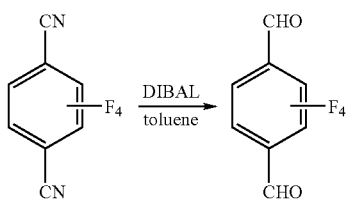

(5)

Example 3

Preparation of α,α,α',α'-tetrafluoro-2,3,5,6-tetrafluoroxylene

About 0.84 g (about 4.08 mmol) of tetrafluorophthaldehyde prepared as described in Example 2 was added to about 20 mL of dry dichloromethane.

The mixture was cooled to about 0° C. under a $N_2$ atmosphere.

About 1.6 mL (about 12.2 mmol) of a fluorinating agent, diethyl aminosulfur trifluoride (DAST), in about 5 mL of the dichloromethane was added drop by drop.

After the addition, the mixture was brought to room temperature for about six hours and then poured into about 100 mL of ice-water.

The organic layer was washed with an about 5% sodium hydroxide solution.

The crude mixture was flash chromatographed with hexane providing an about 60% yield of α,α,α',α'-tetrafluoro-2,3,5,6-tetrafluoroxylene.

The $^1$H NMR resonance of the α,α,α',α'-tetrafluoro-2,3,5,6-tetrafluoroxylene product in $CDCl_3$ was δ 6.952 (t, 2H), and the $^{19}$F NMR resonance was δ −115.19 (4F, d, J=50 Hz), −115.282 (2F, d), −142.17 (s, 4F). The melting point of the product was about 70° C.

The reaction scheme (6) is illustrated below.

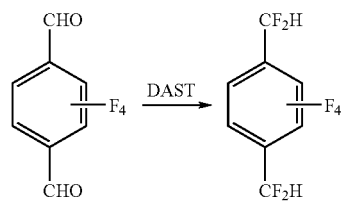

(6)

Example 4

Synthesis of α,α'-dichloro-α,α,α',α'-tetrafluoro-2,3,5,6-tetrafluoroxylene

About 26 g (about 0.104 mol) of α,α,α',α'-tetrafluoro-2,3,5,6-tetrafluoroxylene was dissolved in about 400 mL of carbon tetrachloride.

Chlorine gas was bubbled through the mixture for about 56 hours at 60° C.

A tungsten sunlamp was used to irradiate the mixture.

The reaction was monitored by checking the $^{19}$F NMR resonance.

The mixture was cooled and white precipitate was filtered.

The carbon tetrachloride carrier was carefully removed by rotary evaporation.

The residue was distilled under vacuum, at about 0.2 mm Hg and about 30° C., to yield α,α'-dichloro-α,α,α',α'-tetrafluoro-2,3,5,6-tetrafluoroxylene product, which was found to have a $^{19}$F NMR resonance in $CDCl_3$ of δ −47.61 (m, 4F), −137.88 (m, 4F). The product was further analyzed by GC-EI-MS to be $C_8F_8Cl_2$, 319; $C_8F_8Cl$, 283, and $C_8F_8$, 248.

The reaction scheme (7) is illustrated below.

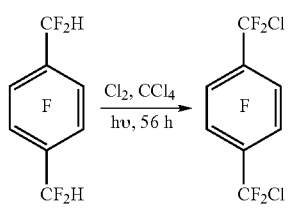

(7)

Example 5

Preparation of perfluoro-paracyclophane (AF8)

About 2 g (about 6.27 mmol) of α,α'-dichloro-α,α,α',α'-tetrafluoro-2,3,5,6-tetrafluoroxylene was added to about 1.63 g (about 25 mmol) of zinc (about 99.7%) in about 20 mL of acetonitrile.

The mixture was refluxed at about 115° C.) for about fourteen hours under nitrogen.

Another about 0.27 g of zinc and about 5 mL of acetonitrile were added.

The mixture was refluxed for another four hours to reach about 100% conversion.

The reaction mixture was hot filtered and washed several times with acetonitrile and acetone.

The combined filtrate was dried by rotary evaporation.

The crude mixture was flash chromatographed with hexane through silica gel as the stationary phase to yield about 0.4 g of crude product.

The crude product was recrystalized with dichloromethane twice, and also with acetone to yield about 0.3 g (about 25%) of product with a purity of about 95%.

The crude product was analyzed and determined to have a melting point in a range of about 195 to 196° C.; a $^{19}$F NMR resonance in $CDCl_3$ of δ −102.81 (s, 4F), −132.40 (s, 4F). The crude product was further analyzed by mass spectrometry to be 496 of $C_{16}F_{16}$, and 248 of $C_8F_8$.

The insoluble residue was then treated with about 4M HCl until bubbling stopped. The AF8 product was then collected and extracted in a Soxhlet extractor with acetone as the solvent. GPC analysis showed that the solution contained some oligomers with a $M_n$ of about 2,000.

The overall reaction scheme (8) is illustrated below.

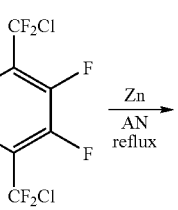

(8)

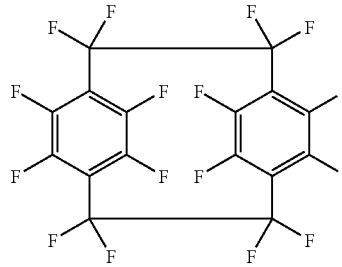

In addition to the reaction product (II), zinc reduction of α,α'-dichloro-α,α,α',α'-tetrafluoro-2,3,5,6-tetrafluoroxylene (PFPX-dichloride) in scheme (8) can result in the byproducts (III) and (IV).

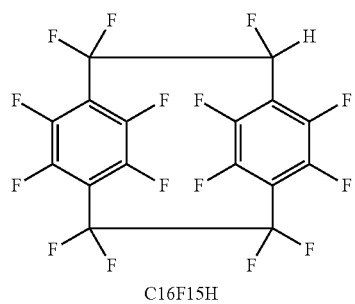

C16F15H
-201 ppm

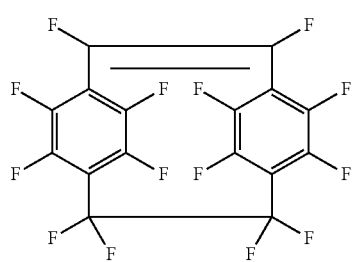

C16F14
-103.625 ppm, 4F,
-122.57 ppm, 2F,
-129.37 ppm(d, 4F)
-134.01 ppm(4F)

Other solvents that may be utilized instead of, or in combination with the solvents listed above include, but are not limited to, acetonitrile, anisole, 2-butanone, 1,4-dioxane, benzonitrile, succinonitrile, and acetic anhydride. Alternative reducing agents may be used including, for example, trimethylsilyltributyltin (TMSTBT, Me₃SiSnBu₃).

Table 1 below shows the results utilizing various reducing agents and solvents in scheme (8).

TABLE 1

| Solvent | Reaction Conditions | Observations |
|---|---|---|
| anisole | 170° C. | about 5% AF8 product |
|  | 20 hours | about 90% SM byproduct |
| 2-butanone | 110° C. | about 10% AF8 |
|  | 20 hours | about 10% SM |
|  |  | 80% impurities |

TABLE 1-continued

| Solvent | Reaction Conditions | Observations |
|---|---|---|
| 1,4-dioxane | 130° C. | about 8% AF8 |
|  | 5 hours | about 82% SM |
| 1,4-dioxane | 130° C. | all byproduct |
|  | 13 hours |  |
| benzonitrile | 110° C. | AF8 product |
|  | overnight |  |
| sulpholane | 100° C. | no reaction |
|  | 7 hours |  |
| sulpholane | 150° C. | SM byproduct |
|  | 15 hours |  |
| TiCl₄ (5 mol %) | 0° C. | no reaction |
| 1,4-dioxane | 2 hours |  |
| TiCl₄ (5 mol %) | room temperature | no reaction |
| 1,4-dioxane | 2 hours |  |
| TiCl₄ (5 mol %) | 130° C. | no reaction |
| 1,4-dioxane | 2 hours |  |
| TiCl₄ (5 mol %) | 130° C. | 100% byproduct |
| 1,4-dioxane | 20 hours |  |
| succinonitrile | 140° C. | black, solidified |
|  | 18 hours | trace amount of SM byproduct |
| TMSTBT, CsF | 70° C. | CF₃ peak observed |
| DMSO/THF (1:4) | 48 hours | SM byproduct |
| Zn—Cu couple | 130° C. | trace AF8 product |
| acetonitrile | 20 hours |  |
| DMA (8%)/AN | 80° C. | no reaction |
|  | 1 hour |  |
| DMA (8%)/AN | 80° C. | decomposed |
|  | 18 hours |  |
| NaI | room temperature | SM byproduct |
| DME | 18 hours |  |
| NaI | 80° C. | SM byproduct |
| DME | 18 hours |  |
| Diglycol dimethyl | 160° C. | no product |
|  | 20 hours |  |
| HgCl₂ (5 mol %) | 20 hours | trace AF8 product |
| then Ag(OTf)₂/AN |  | SM byproduct and impurities |
| Ag(OAc) | 140° C. | no product |
| toluene |  |  |
| Ac₂O | 80° C. | hydrolyzed reactants |

Example 6

Synthesis of perfluoro-paraxylene monomer

In each of the following reduction reactions, about 5 mL of the indicated solvent was used.

(a) About 1 g of α,α'-dichloro-α,α,α',α'-tetrafluoro-2,3,5,6-tetrafluoroxylene was reduced 100% to perfluoro-paraxylene product by zinc (4eq) at a temperature of about 100° C. in dimethylacetamide (DMA) and the product was further brominated overnight according to the reaction scheme (9) below.

The monomer peak was observed at −101.536 ppm. 4 F peak was noted at −146.377 ppm.

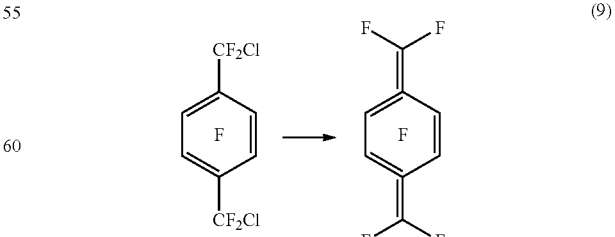

(b) Dichloro-tetrafluoro-paraxlylene was 100% reduced to the monomer product by zinc in 1,3-dimethyl-2-imidazolidinone (DMI), instead of DMA, at a temperature of about 80° C. to about 90° C. for about thirty minutes as in scheme (9).

A $CF_3$ byproduct peak was noted at −57.5 ppm.

(c) Dichloro-tetrafluoro-paraxylene was also reduced by zinc in hexamethlyphosphoramide (HMPA), instead of DMA, at a temperature of about 80° C. to about 90° C. for about thirty minutes, to the perfluoro-paraxlylene product as in scheme (9). Byproduct peaks were noted at −82.326 ppm, −85.677 ppm, and −141.781 ppm.

(d) N-methylpyrrolidone (NMP) was used as a solvent instead of DMA in scheme (9) to facilitate zinc reduction of α,α'-dichloro-α,α,α',α'-tetrafluoro-2,3,5,6-tetrafluoroxylene into perfluoro-paraxlylene monomer. The reaction was also performed at 80° C. for about thirty minutes.

(e) α,α'-dichloro-α,α,α',α'-tetrafluoro-2,3,5,6-tetrafluorooxylene was 100% reduced by zinc overnight at room temperature in dimethyl sulfoxide (DMSO) to a solvent stabilized perfluoro-paraxylene monomer, $^{19}F$ NMR −101.54 ppm, 4 F; −146.38 ppm, 4 F, absorption maximum at 290 nm in DMSO solution.

The monomer was observed to be stable at room temperature in the NMR tube even after one week.

The monomer was preserved or trapped by slow addition of bromine to form α,α'-dibromo-α,α,α',α'-tetrafluoro-2,3,5,6-tetrafluorooxylene, −43.773 ppm, m, 4 F; −137.852 ppm, m, 4 F and M/Z:M-Br, 327, M-2Br, 248.

Having now described various embodiments of the invention, it should be apparent to those skilled in the art that the foregoing is merely illustrative and not limiting. Numerous modifications and other embodiments are within the scope of one of ordinary skill in the art and are contemplated as falling within the scope of the invention. Although many of the examples presented herein involve specific combinations of method acts or features, it should be understood that those acts and those features may be combined in other ways to accomplish the same objectives. However, acts, elements, and features discussed only in connection with one embodiment are not intended to be excluded from a similar role in other embodiments. Moreover, it should also be appreciated that the invention is directed to each feature, system, subsystem, or technique described herein and any combination of two or more features, systems, subsystems, or techniques described herein and any combination of two or more features, systems, subsystems, and/or methods, if such features, systems, subsystems, and techniques are not mutually inconsistent, is considered to be within the scope of the invention as embodied in the claims.

Use of ordinal terms such as "first," "second," "third," and the like in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. As used herein, the term "plurality" refers to two or more items or components. The terms "comprising," "including," "carrying," "having," "containing," and "involving," whether in the written description or the claims and the like, are open-ended terms, i.e., to mean "including but not limited to." Thus, the use of such terms is meant to encompass the items listed thereafter, and equivalents thereof, as well as additional items. Only the transitional phrases "consisting of" and "consisting essentially of," are closed or semi-closed transitional phrases, respectively, with respect to the claims.

Those skilled in the art should appreciate that the parameters and configurations described herein are exemplary and that actual parameters and/or configurations will depend on the specific application in which the systems and techniques of the invention are used. Those skilled in the art should also recognize or be able to ascertain, using no more than routine experimentation, equivalents to the specific embodiments of the invention. It is therefore to be understood that the embodiments described herein are presented by way of example only and that, within the scope of the appended claims and equivalents thereto; the invention may be practiced otherwise than as specifically described.

What is claimed is:

1. A method of preparing a perfluoroparacyclophane comprising exposing a reaction mixture comprising bis-chlorodifluoromethyl-tetrafluorobenzene, a solvent comprising at least one selected from the group consisting of an organic nitrile, anisole, and dioxane, and at least one metal to conditions that promote formation of a reaction product comprising the perfluoroparacyclophane represented by the formula:

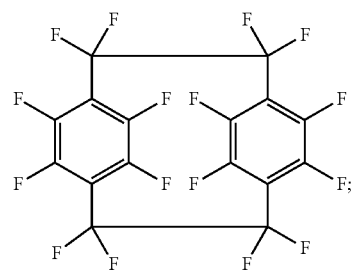

and recovering the reaction product.

2. The method of claim 1, wherein the solvent comprises acetonitrile.

3. The method of claim 2, wherein the at least one metal is at least one of a transition metal, zinc, mercury, and cadmium.

4. The method of claim 2, wherein the at least one metal is zinc.

5. The method of claim 4, wherein the reaction mixture is exposed to a temperature of about 120° C.

6. The method of claim 1, wherein the solvent is acetonitrile and the at least one metal is zinc.

7. A method of preparing perfluoroparacyclophane comprising:
   refluxing a mixture comprising α,α'-dichloro-α,α,α',α'-tetrafluoro-2,3,5,6-tetrafluoroxylene, zinc, and acetonitrile to produce a crude product;
   recrystallizing the crude product with at least one of dichloromethane and acetone to produce a perfluoroparacyclophane product represented by the formula

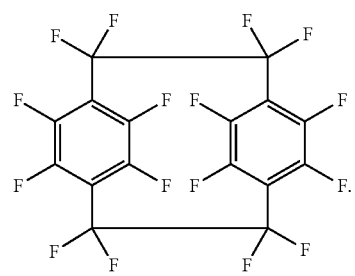

8. The method of claim 7, further comprising exposing the crude product to hydrochloric acid to produce the perfluoroparacyclophane product.

9. The method of claim 8, further comprising filtering a product mixture of the refluxing step to produce a filtrate comprising the crude product.

10. The method of claim 9, wherein recrystallizing the crude product comprises recrystallizing the crude product with a solvent comprising dichloromethane.

11. The method of claim 10, wherein refluxing the mixture comprises refluxing the mixture at a temperature of about 115° C.

12. The method of claim 1, wherein exposing the reaction mixture comprises refluxing the reaction mixture under a nitrogen atmosphere.

13. The method of claim 12, further comprising washing a product of the reaction mixture with acetonitrile and acetone.

14. The method of claim 1, wherein recovering the reaction product comprises extracting the reaction product with acetone.

* * * * *